United States Patent
Fujii

(10) Patent No.: US 10,519,677 B2
(45) Date of Patent: Dec. 31, 2019

(54) ACTUATOR AND FORCE DRIVING MECHANISM FOR TREATMENT TOOL

(71) Applicant: OLYMPUS CORPORATION, Tokyo (JP)

(72) Inventor: Masahiro Fujii, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 330 days.

(21) Appl. No.: 15/667,662

(22) Filed: Aug. 3, 2017

(65) Prior Publication Data

US 2018/0112422 A1 Apr. 26, 2018

Related U.S. Application Data

(63) Continuation of application No. PCT/JP2016/081232, filed on Oct. 21, 2016.

(51) Int. Cl.
| | |
|---|---|
| *E04G 21/12* | (2006.01) |
| *B65B 13/28* | (2006.01) |
| *A61B 90/00* | (2016.01) |
| *A61B 17/00* | (2006.01) |

(52) U.S. Cl.
CPC .......... *E04G 21/123* (2013.01); *B65B 13/285* (2013.01); *A61B 2017/00327* (2013.01); *A61B 2017/00398* (2013.01); *A61B 2090/064* (2016.02)

(58) Field of Classification Search
CPC ... F16H 21/44; F16H 21/50; A61B 17/22031; A61B 17/29; A61B 17/28; A61B 2090/064; A61B 2017/00398; A61B 2017/00327; E04G 21/123; E04G 21/12; B65B 13/285

See application file for complete search history.

(56) References Cited

U.S. PATENT DOCUMENTS

| | | | | |
|---|---|---|---|---|
| 3,895,636 A | * | 7/1975 | Schmidt ................. | A61B 10/06 606/205 |
| 5,133,727 A | * | 7/1992 | Bales ..................... | A61B 17/29 606/170 |
| 5,281,230 A | * | 1/1994 | Heidmueller .......... | A61B 17/29 604/902 |

(Continued)

FOREIGN PATENT DOCUMENTS

| | | |
|---|---|---|
| JP | S64-26017 A | 2/1989 |
| JP | 2010-227600 A | 10/2010 |

*Primary Examiner* — Phong Son H Dang
(74) *Attorney, Agent, or Firm* — Scully, Scott, Murphy & Presser, P.C.

(57) ABSTRACT

An actuator for a treatment tool including: a tube having a distal end configured to rotatably support the treatment tool; a twisting wire disposed along a longitudinal axis of the tube, the twisting wire having a distal end and a proximal end, the treatment tool being connected to the distal end of the twisting wire, the twisting wire being actuated by applying a tensile force at the proximal end, the twisting wire converting the tensile force into rotation of the treatment tool around the longitudinal axis of the tube; and at least one wire movable in a longitudinal direction to actuate the treatment tool, the at least one wire actuating the treatment tool separately from actuation of the twisting wire to rotate the treatment tool.

12 Claims, 5 Drawing Sheets

(56) References Cited

U.S. PATENT DOCUMENTS

| | | | |
|---|---|---|---|
| 5,433,721 A * | 7/1995 | Hooven | A61B 17/068 227/175.1 |
| 5,439,478 A * | 8/1995 | Palmer | A61B 1/00087 606/205 |
| 6,027,522 A * | 2/2000 | Palmer | A61B 10/06 606/205 |
| 6,358,256 B1 * | 3/2002 | Reinhardt | A61N 1/057 606/108 |
| 7,147,650 B2 * | 12/2006 | Lee | A61B 17/00234 606/205 |
| 8,162,973 B2 * | 4/2012 | Cunningham | A61B 17/29 606/205 |
| 8,221,306 B2 * | 7/2012 | Okada | A61B 1/00071 600/106 |
| 8,721,657 B2 * | 5/2014 | Kondoh | A61B 17/3478 600/146 |
| 8,771,260 B2 * | 7/2014 | Conlon | A61B 17/29 606/1 |
| 9,155,586 B2 * | 10/2015 | Suzuki | A61B 18/1445 |
| 9,277,932 B2 * | 3/2016 | Slater | A61B 17/320016 |
| 9,566,082 B2 * | 2/2017 | Slater | A61B 17/295 |
| 9,770,256 B2 * | 9/2017 | Cohen | A61B 17/295 |
| 9,877,794 B2 * | 1/2018 | Csiky | A61B 17/062 |
| 10,188,415 B2 * | 1/2019 | Ishii | A61B 17/29 |
| 10,238,411 B2 * | 3/2019 | Mitelberg | A61B 1/018 |
| 10,383,647 B2 * | 8/2019 | Ishida | A61B 17/29 |
| 2002/0010485 A1 * | 1/2002 | Griego | A61B 17/32056 606/167 |
| 2002/0177888 A1 * | 11/2002 | Williams | A61N 1/056 607/122 |
| 2007/0260114 A1 * | 11/2007 | Miyamoto | A61B 17/29 600/114 |
| 2008/0051694 A1 * | 2/2008 | Kato | A61B 1/00071 604/22 |
| 2009/0137872 A1 * | 5/2009 | Bahney | A61B 1/018 600/118 |
| 2009/0216245 A1 * | 8/2009 | Viola | A61B 1/00147 606/108 |
| 2011/0022144 A1 * | 1/2011 | Jarl | A61N 1/056 607/127 |
| 2011/0106073 A1 * | 5/2011 | Mueller | A61B 17/29 606/41 |
| 2011/0319888 A1 * | 12/2011 | Mueller | A61B 18/1445 606/41 |
| 2015/0105798 A1 * | 4/2015 | Lohmeier | A61B 34/71 606/130 |
| 2016/0345995 A1 * | 12/2016 | Takei | A61B 17/29 |
| 2019/0167239 A1 * | 6/2019 | Okabe | A61B 17/00 |

* cited by examiner

ACTUATOR AND FORCE DRIVING MECHANISM FOR TREATMENT TOOL

CROSS-REFERENCE TO RELATED APPLICATIONS

This is a continuation of International Application PCT/JP2016/081232, with an international filing date of Oct. 21, 2016, which is hereby incorporated by reference herein in its entirety.

TECHNICAL FIELD

The present invention relates to an actuator and a force driving mechanism for a treatment tool.

BACKGROUND ART

In a treatment tool that operates a treatment section disposed in a distal end of an elongated member formed of a coil sheath to be inserted into a body by traction of a wire, a technology for making the winding direction of the coil sheath and the twisting direction of the wire coincide with each other to rotate the treatment section around the longitudinal axis of the elongated member by utilization of recovery of the twist of the wire due to tractive power is known (for example, refer to PTL 1).

In a technology of PTL 1, only in a state where the treatment section is operated, for example, only in a state where grasping forceps is closed in a case where the treatment section is the grasping forceps, the treatment section can be rotated.

CITATION LIST

Patent Literature

{PTL 1} Japanese Unexamined Utility Model Application, Publication No. sho64-26017

SUMMARY OF INVENTION

An aspect of the present invention is an actuator for a treatment tool, the actuator including: a tube having a distal end configured to rotatably support the treatment tool; a twisting wire disposed along a longitudinal axis of the tube, the twisting wire having a distal end and a proximal end, the treatment tool being connected to the distal end of the twisting wire, the twisting wire being actuated by applying a tensile force at the proximal end, the twisting wire converting the tensile force into rotation of the treatment tool around the longitudinal axis of the tube; and at least one wire movable in a longitudinal direction to actuate the treatment tool, the at least one wire actuating the treatment tool separately from actuation of the twisting wire to rotate the treatment tool.

Another aspect of the present invention is a force driving mechanism for a treatment tool, the force driving mechanism comprising: an elongated member for supporting the treatment tool; a first drive means connected to the treatment tool, for rotating the treatment tool around a longitudinal axis of the elongated member by pulling the first drive means; and a second drive means disposed separately from the first drive means and connected to the treatment tool, for actuating the treatment tool by pulling the second drive means.

DESCRIPTION OF EMBODIMENTS

Hereinafter, a force driving mechanism and an actuator 1 for a treatment tool according to an embodiment of the present invention will be described with reference to the drawings.

The actuator 1 for a treatment tool according to this embodiment is a mechanism for rotating a treatment tool 3 mounted in a distal end of a flexible elongated tube 2 around the longitudinal axis of the tube 2 by operation on a proximal end side of the tube 2.

Figure 1:
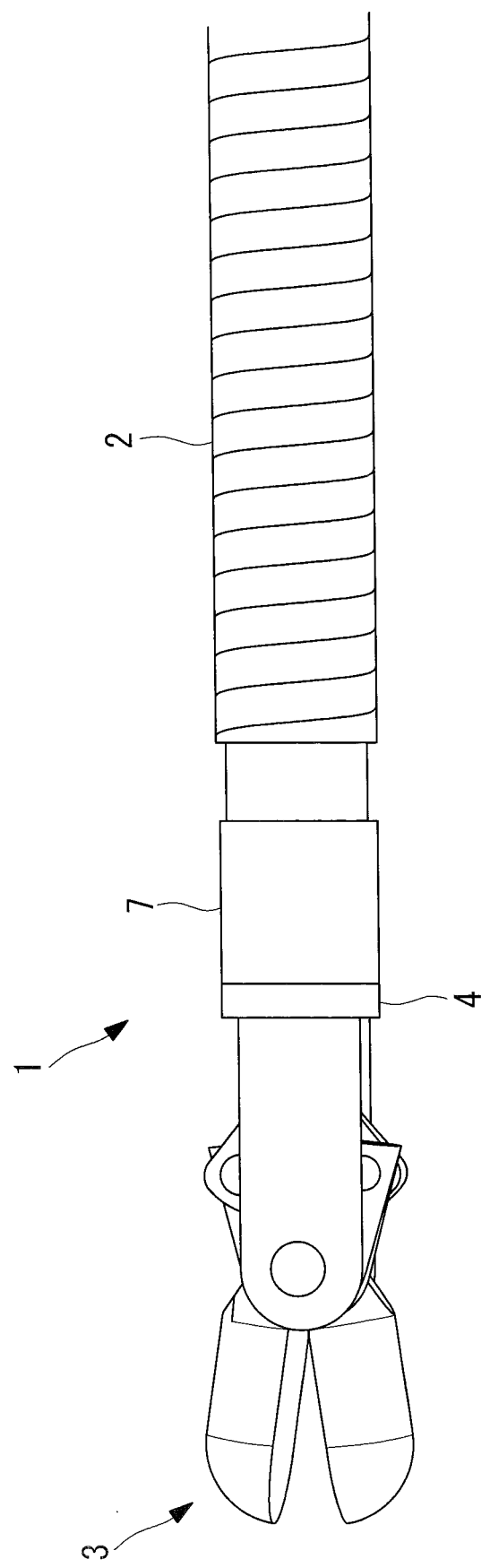
FIG. 1 is a partial side view illustrating an actuator for a treatment tool according to an embodiment of the present invention.
Figure 2:
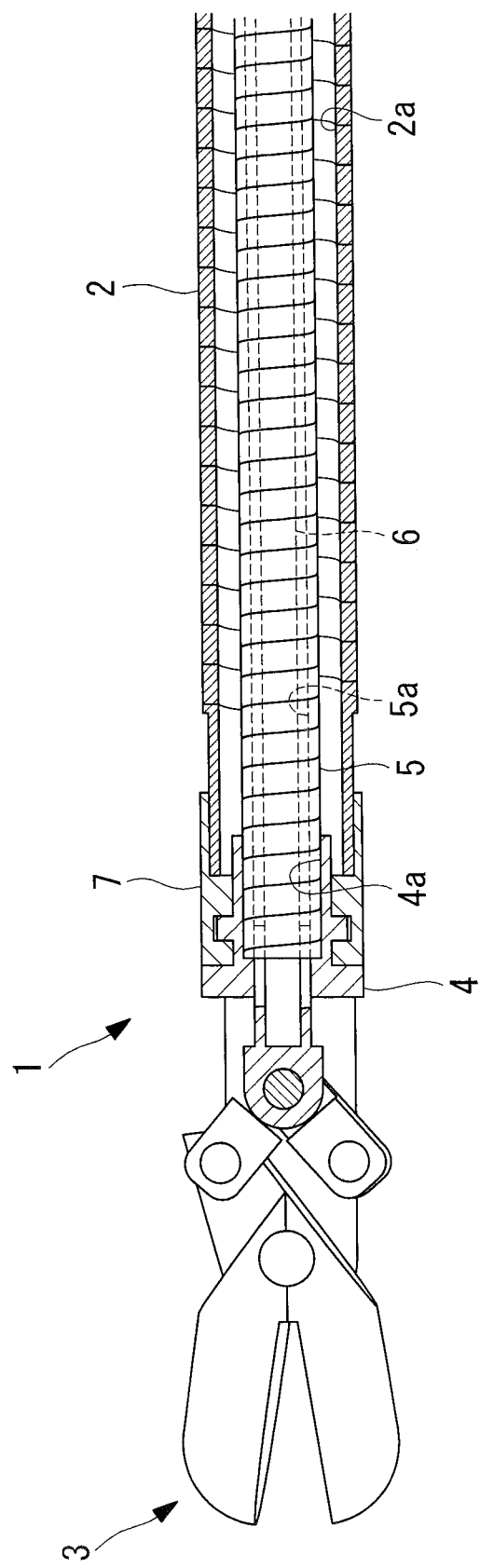
FIG. 2 is a longitudinal sectional view illustrating the actuator for a treatment tool in FIG. 1.

As illustrated in FIG. 1 and FIG. 2, the actuator 1 for a treatment tool according to this embodiment includes the flexible tube (elongated member) 2, a cylindrical rotator 4 rotatably supported around the longitudinal axis on the distal end of the tube 2, and a flexible tubular twisting wire (a first drive means) 5 that is disposed over the whole length of the tube 2 to pass through a central hole (through hole) 2a of the tube 2, and has a distal end to which the rotator 4 is fixed.

The tube 2 is preferably a sheath formed of a wound coil (coil sheath).

The treatment tool 3 is, for example, a grasping forceps having tow movable jaws. The jaws are configured to be actuated by pulling a flexible wire (a second drive means) 6 connected to the treatment tool 3.

A treatment tool 3 is fixed to the rotator 4, and the wire 6, for supplying power, that transmits tensile force for operating the treatment tool 3 passes through central holes (through holes) 4a and 5a of the rotator 4 and the twisting wire 5 to be led to the proximal end side of the tube 2.

To the distal end of the tube 2, a cylindrical member (receiving member) 7 against which a surface on the proximal end side of the rotator 4 abuts in the longitudinal axis direction and which rotatably supports the rotator 4 around the longitudinal axis is fixed.

The twisting wire 5 shifts in the direction in which the twisting wire 5 is untwisted when a tensile force of a predetermined size or greater is generated by tractive power applied by manual operation or an actuator (not illustrated) on the proximal end side of the tube 2. Consequently, in the twisting wire 5, rotation force around the longitudinal axis is generated in the twisting direction. That is, the twisting wire 5 converts the tractive power along the longitudinal direction applied to a proximal end of the twisting wire 5 into rotation force around the longitudinal axis in a distal end of the twisting wire 5.

The rotation force converted from the tensile force by the twisting wire 5 can rotate the rotator 4 fixed to the distal end of the twisting wire 5 around the longitudinal axis, and rotate the treatment tool 3 fixed to the rotator 4 around the longitudinal axis.

Action of thus configured actuator 1 for a treatment tool according to this embodiment will be hereinafter described.

According to the actuator 1 for a treatment tool according to this embodiment, when tractive power for pulling the twisting wire (a first drive means) 5 toward the proximal end side is applied on the proximal end side of the tube 2, tensile force generated in the twisting wire 5 is transmitted to the rotator 4 at the distal end of the tube 2, and the rotator 4 is pulled toward the proximal end side. The rotator 4 axially abuts against the cylindrical member 7, and therefore the rotator 4 does not axially move, and the tensile force generated in the twisting wire 5 is increased.

Then, when the tensile force generated in the twisting wire 5 becomes a force of a predetermined size or greater, the twisting wire 5 shifts in the direction in which the twisting wire 5 is untwisted, and therefore rotation force in the direction in which the twisting wire 5 is twisted is generated in the distal end of the twisting wire 5. The rotator 4 fixed to the distal end of the twisting wire 5 is rotatably supported around the longitudinal axis with respect to the cylindrical member 7 fixed to the distal end of the tube 2, and therefore is rotated around the longitudinal axis by the rotation force generated in the distal end of the twisting wire 5. Consequently, the treatment tool 3 fixed to the rotator 4 is also rotated around the longitudinal axis.

When the twisting wire 5 is twisted by rotating of the rotator 4, the tensile force generated in the twisting wire 5 is released, and therefore rotation of the rotator 4 is stopped at this position. In a case where the treatment tool 3 is desired to be further rotated, the tractive power for pulling the proximal end of the twisting wire 5 toward the proximal end side is applied again, so that the treatment tool 3 can be rotated around the longitudinal axis in the same direction again.

Then, the wire 6 for operating the treatment tool 3 passes through the central hole 5a of the tubular twisting wire 5, and is drawn out on the proximal end side of the tube 2. Therefore, the treatment tool 3 can be operated by tractive power applied to the wire 6 separate from the tractive power applied to the twisting wire 5.

Thus, according to the actuator 1 for a treatment tool according to this embodiment, there is an advantage that the treatment tool 3 disposed in the distal end of the tube 2 can be rotated around the longitudinal axis of the tube 2 without being operated.

That is, when the grasping forceps as the treatment tool 3 is rotated around the longitudinal axis, the grasping forceps can be rotated in a state where the grasping forceps is opened, and the direction of the grasping forceps at the time of approaching a site to be grasped can be easily changed.

Figure 3:
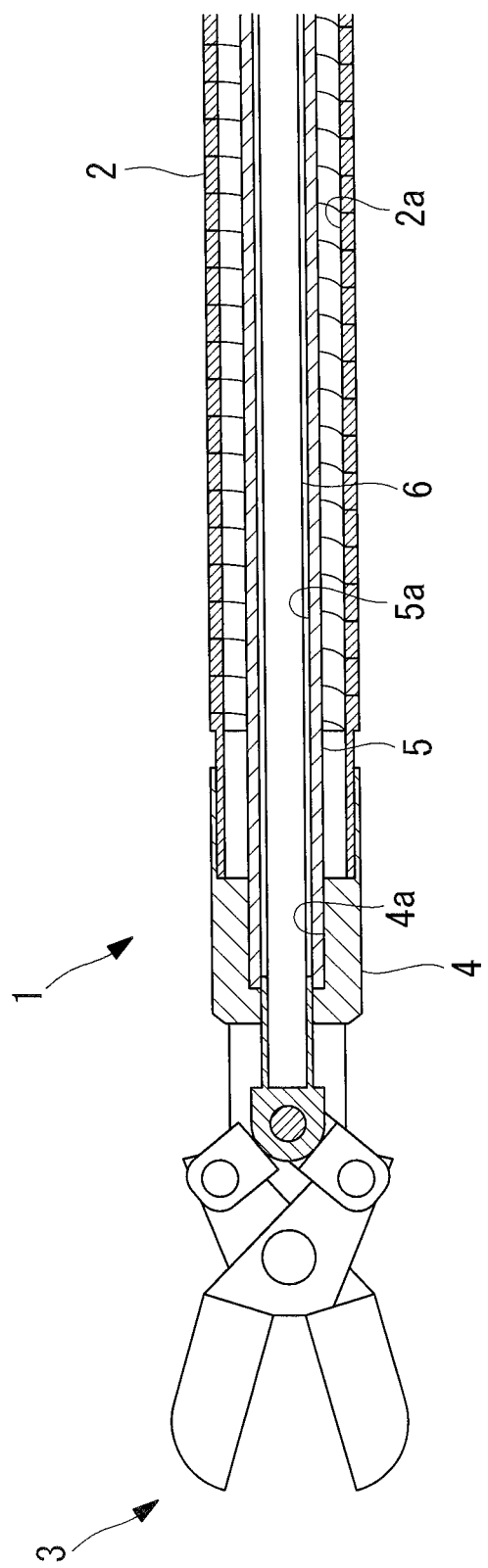
FIG. 3 is a longitudinal sectional view illustrating a modification of the actuator for a treatment tool in FIG. 2.

In this embodiment, the rotator 4 is rotatably supported around the longitudinal axis with respect to the cylindrical member 7 fixed to the distal end of the tube 2. However, alternatively, as illustrated in FIG. 3, the rotator 4 may be fixed to the distal end of the tube 2 by making the twisting direction of the twisting wire 5 and the winding direction of the tube 2 coincide with each other.

Thus, shift in the untwisting direction by the tensile force causes the rotation force generated in the distal end of the twisting wire 5 to act in the direction in which winding of the tube 2 is unwound, so that the tube 2 itself can be twisted around the longitudinal axis, and the rotator 4 and the treatment tool 3 fixed to the distal end can be rotated around the longitudinal axis.

Figure 4:
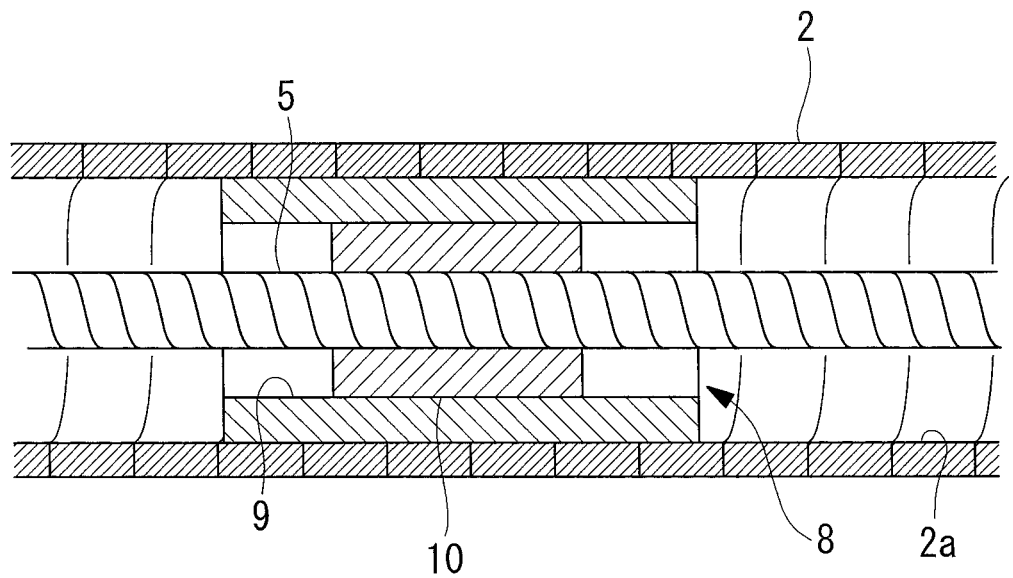
FIG. 4 is a partial longitudinal sectional view illustrating a rotation stopper of the modification of the actuator for a treatment tool in FIG. 1.
Figure 5:
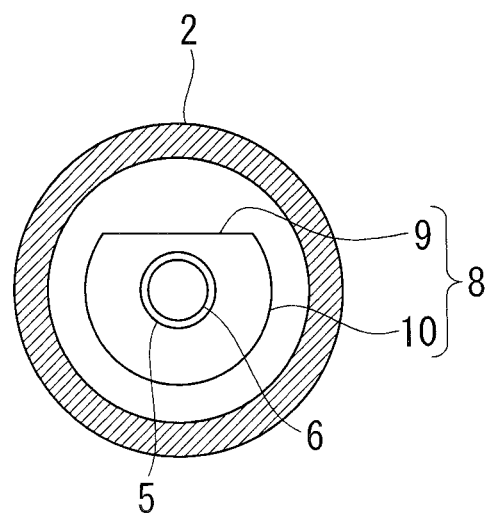
FIG. 5 is a front view illustrating a cross sectional shape of the rotation stopper in FIG. 4.

In this embodiment, a rotation stopper 8 that allows relative movement in the longitudinal axis direction between the tube 2 and the twisting wire 5, and locks rotation around the longitudinal axis between the tube 2 and the twisting wire 5 may be provided at a position spaced on the proximal end side in the longitudinal axis direction from the distal ends of the tube 2 and the twisting wire 5, as illustrated in FIG. 4 and FIG. 5.

As an example of the rotation stopper 8, a rotation stopper composed of a recess portion (a first portion) 9 fixed to an inner surface of the tube 2 and extending in the longitudinal axis direction, and a projection portion (a second portion) 10 fixed to an outer surface of the twisting wire 5 and fitted in the recess portion 9 can be employed.

The recess portion 9 has a non-circular constant cross sectional shape, and the projection portion 10 has a cross sectional shape which is complementary to the recess portion 9.

As illustrated in FIG. 5, the cross sectional shapes of the recess portion 9 and the projection portion 10 each may be a shape formed by cutting out a part of a circle by a plane.

Consequently, at positions of the projection portion 10 and the recess portion 9, namely, at a position of the rotation stopper 8, the tube 2 and the twisting wire 5 can relatively move in the longitudinal axis direction, but cannot relatively rotate around the longitudinal axis.

Thus, when the tractive power is applied to the proximal end of the twisting wire 5, the tensile force is generated in the twisting wire 5 on the proximal end side with respect to the rotation stopper 8, and the twisting wire 5 moves to the proximal end side in the longitudinal axis direction relatively to the tube 2, but relative rotation is locked by the rotation stopper 8. Therefore, rotation is not generated in the twisting wire 5. On the other hand, tensile force transmitted by the twisting wire 5 on the proximal end side acts on the twisting wire 5 on the distal end side with respect to the rotation stopper 8, and therefore when the tensile force becomes a force of a predetermined size or greater, the rotator 4 and the treatment tool 3 fixed to the distal end of the twisting wire 5 can be rotated with respect to the tube 2.

That is, in a case where a route to an object to be treated winds, frictional force is generated between the twisting wire 5 and the tube 2 being curved, and rotation force is unlikely to be transmitted. However, relative rotation around the longitudinal axis between the tube 2 and the twisting wire 5 is not generated on the proximal end side with respect to the rotation stopper 8, and therefore there is an advantage that an influence of frictional force is hardly received. Additionally, the tensile force transmitted by the twisting wire 5 on the proximal end side with respect to the rotation stopper 8 is converted into rotation force by the twisting wire 5 on the distal end side with respect to the rotation stopper 8, so that the treatment tool 3 can be more reliably rotated.

Figure 6:
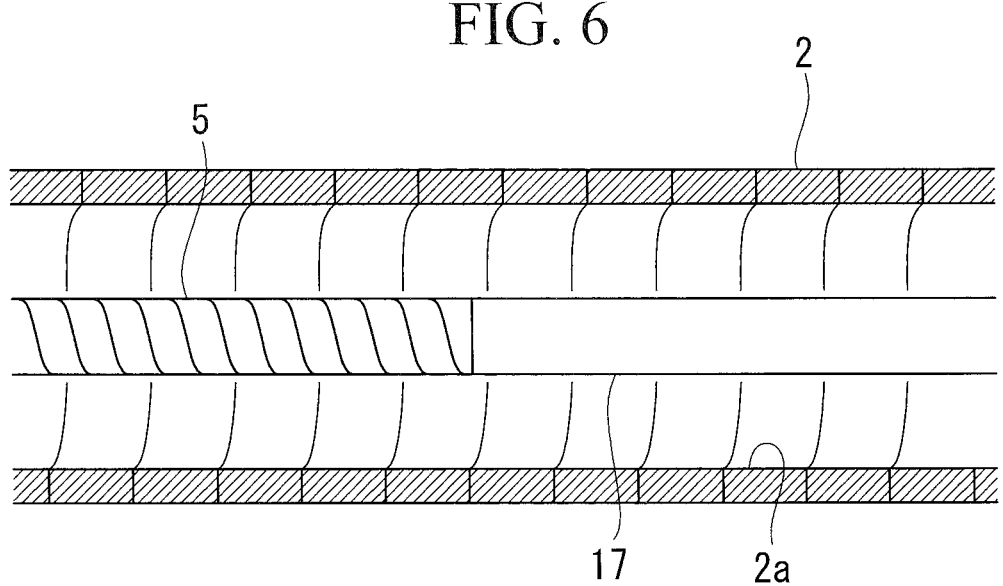
FIG. 6 is a partially longitudinal sectional view illustrating a modification of the rotation stopper in FIG. 4.

In place of the rotation stopper 8, as illustrated in FIG. 6, the distal ends of the twisting wire 5 may be disposed at a position between the distal and proximal ends of the tube 2, and an untwisted tube 17 may be joined to the proximal end side of the twisting wire 5.

Additionally, in place of the rotation stopper 8, the tube 2 may be formed such that torsional rigidity is changed at an intermediate position in the longitudinal axis direction. In this case, in order to change torsional rigidity of the tube 2, for example, the tube (coil sheath) may be formed of different materials or a coating member for coating an outer peripheral surface on the proximal end side of the tube 2 may be removed on the distal end side, such that torsional rigidity on the distal end side becomes smaller than torsional rigidity on the proximal end side.

In this embodiment, the recess portion 9 and the projection portion 10 have the constant cross sectional shape formed by cutting out a part of a circle by a plane. However, alternatively, other arbitrary non-circular cross sectional shapes may be employed like a recess portion 9 having a circular cross sectional shape having a key groove (not illustrated), and a columnar cylindrical projection portion 10 having a key (not illustrated).

As the treatment tool 3, grasping forceps is exemplified. However, other arbitrary treatment tool may be employed.

Additionally, a treatment tool provided with a joint is employed, the wire 6 leading through the central holes 4a and 5a of the tubular twisting wire 5 and rotator 4 may drive the joint.

From the above-described embodiment and modifications thereof, the following aspects of the invention are derived.

An aspect of the present invention is an actuator for a treatment tool, the actuator including: a tube having a distal end configured to rotatably support the treatment tool; a twisting wire disposed along a longitudinal axis of the tube, the twisting wire having a distal end and a proximal end, the treatment tool being connected to the distal end of the twisting wire, the twisting wire being actuated by applying a tensile force at the proximal end, the twisting wire converting the tensile force into rotation of the treatment tool around the longitudinal axis of the tube; and at least one wire movable in a longitudinal direction to actuate the treatment tool, the at least one wire actuating the treatment tool separately from actuation of the twisting wire to rotate the treatment tool.

According to this aspect, when tractive power is applied to the proximal end side of the twisting wire, the tensile force applied to the twisting wire is converted in force for rotating the distal end around the longitudinal axis. Specifically, when a tensile force of a predetermined size or greater acts on the twisting wire, the twisting wire shifts in the direction in which the twisting wire is untwisted. As a result, circumferential rotation force is generated in the twisting direction, and the distal end of the twisting wire is rotated around the longitudinal axis by the generated rotation force. Additionally, when the tensile force applied to the twisting wire is relaxed, the twisting wire is twisted again.

Consequently, the treatment tool connected to the distal end of the twisting wire is rotated around the longitudinal axis.

The at least one wire is separately provided from the twisting wire, and power for operating the treatment tool is supplied to the treatment tool through the at least one wire.

That is, according to this aspect, the mechanism that rotates the treatment tool around the longitudinal axis and the at least one wire that supplies power to the treatment tool are independent, and therefore it is possible to rotate the treatment tool around the longitudinal axis without operating the treatment tool.

In the above aspect, the rotator may be fixed to the distal end of the twisting wire, the rotator supporting the treatment tool at the distal end of the tube.

Consequently, the rotator can be rotated around the longitudinal axis with respect to the tube, and a material having high torsional rigidity can be used as the tube.

In the above aspect, at least a portion of the distal end of the tube may be configured to rotate around the longitudinal axis, the tube and the rotator being fixed to each other.

Consequently, when the rotation force is applied to the rotator, the rotation force is transmitted also to the tube to which the rotator is fixed, and at least the portion of the distal end of the tube is twisted around the longitudinal axis. Consequently, rotation of the rotator around the longitudinal axis is allowed, and the treatment tool can be rotated.

In the above aspect, at least one of the twisting wire and the at least one wire may be flexible.

Consequently, the tube and the twisting wire are curved to be inserted into a route such as a winding body cavity, and tractive power is applied to the twisting wire on the proximal end side of the tube, so that the treatment tool can be rotated around the longitudinal axis at the distal end of the tube.

In the above aspect, the tube may be composed of a sheath formed of a wound coil, and a winding direction of the coil of the tube and a winding direction of the twisting wire may coincide with each other.

Consequently, when a tensile force of a predetermined size or greater acts on the twisting wire, the twisting wire shifts in the direction in which the twisting wire is untwisted. As a result, circumferential rotation force is generated in the twisting direction. When the generated rotation force becomes larger than force required for loosening the winding of the wound coil forming the tube, the distal end of the tube is twisted around the longitudinal axis, so that the treatment tool supported by the distal end can be rotated around the longitudinal axis.

In the above aspect, the tube may be flexible.

In the above aspect, the at least one wire may pass through an interior of the twisting wire.

In the above aspect, the actuator may further include the treatment tool. The treatment tool may be a grasping forceps having one or more movable jaws actuated by movement of the at least one wire.

In the above aspect, the actuator may further include a rotation stopper disposed at a position between the distal and proximal ends of the twisting wire, the rotation stopper being configured to permit the twisting wire to move along the longitudinal direction relative to the tube and prohibit the twisting wire from rotating around the longitudinal axis relative to the tube at the position of the rotation stopper.

Consequently, when a tensile force of a predetermined size or greater acts on the twisting wire, the twisting wire shifts in the direction in which the twisting wire is untwisted, so that even when circumferential rotation force is generated in the twisting direction, rotation around the longitudinal axis of the twisting wire with respect to the tube from the proximal end side to the position of the rotation stopper is restricted by the rotation stopper.

On the other hand, the rotation stopper allows relative movement in the longitudinal axis direction of the twisting wire to the tube, and therefore the twisting wire disposed on the distal end side with respect to the rotation stopper also shifts in the untwisting direction, and the distal end of the twisting wire with respect to the tube can be relatively rotated in the twisting direction. Consequently, for example, even when the tube and the twisting wire are disposed in the winding route, so that friction between the tube and the twisting wire is increased, a part of the twisting wire which moves relatively to the tube can be restricted to only a portion on the distal end side with respect to the rotation stopper, and it is possible to rotate the rotator and the treatment tool around the longitudinal axis with respect to the tube without receiving an influence of friction.

In the above aspect, the rotation stopper may include a first portion fixed to an inner surface of the tube, and a second portion fixed to an outer surface of the twisting wire, the second portion being fitted to the first portion.

In the above aspect, the first portion may extend in the longitudinal direction of the tube and have an interior with a first non-circular cross sectional shape, and the second portion may extend in the longitudinal direction of the tube and have an exterior with a second cross sectional shape, wherein the first non-circular cross sectional shape of the first portion may be fitted to with the second cross sectional shape of the second portion.

Consequently, the first portion having the non-circular cross sectional shape, and the second portion having the cross sectional shape which is complementary to the first portion are fitted to each other, so that the tube and the twisting wire can easily be relatively moved in the longitudinal axis direction and be connected relatively unrotatably around the longitudinal axis.

REFERENCE SIGNS LIST 1 actuator for treatment tool
2 tube (elongated member)
2a, 4a, 5a central hole (through hole)
3 treatment tool
4 rotator
5 twisting wire (first drive means)
6 wire (second drive means)
7 cylindrical member (receiving member)
8 rotation stopper
9 recess portion (first portion)
10 projection portion (second portion)

The invention claimed is:

1. An actuator for a treatment tool, the actuator comprising:
   a tube having a distal end configured to rotatably support the treatment tool;
   a twisting wire disposed along a longitudinal axis of the tube, the twisting wire having a distal end and a proximal end, the treatment tool being connected to the distal end of the twisting wire, the twisting wire being actuated by applying a tensile force at the proximal end, the twisting wire converting the tensile force into rotation of the treatment tool around the longitudinal axis of the tube; and
   at least one wire movable in a longitudinal direction to actuate the treatment tool, the at least one wire actuating the treatment tool separately from actuation of the twisting wire to rotate the treatment tool.

2. The actuator according to claim 1, further comprising a rotator fixed to the distal end of the twisting wire, the rotator supporting the treatment tool at the distal end of the tube.

3. The actuator according to claim 2, wherein at least a portion of the distal end of the tube is configured to rotate around the longitudinal axis, the tube and the rotator being fixed to each other.

4. The actuator according to claim 1, wherein at least one of the twisting wire and the at least one wire are flexible.

5. The actuator according to claim 1, wherein the tube comprises a sheath formed of a wound coil, and
   a winding direction of the coil of the tube and a winding direction of the twisting wire coincide with each other.

6. The actuator according to claim 1, wherein the tube is flexible.

7. The actuator according to claim 1, wherein the at least one wire passes through an interior of the twisting wire.

8. The actuator according to claim 1, further comprising the treatment tool.

9. The actuator according to claim 1, wherein the treatment tool is a grasping forceps having one or more movable jaws actuated by movement of the at least one wire.

10. The actuator according to claim 1, further comprising a rotation stopper disposed at a position between the distal and proximal ends of the twisting wire, the rotation stopper being configured to permit the twisting wire to move along the longitudinal direction relative to the tube and prohibit the twisting wire from rotating around the longitudinal axis relative to the tube at the position of the rotation stopper.

11. The actuator according to claim 10, wherein the rotation stopper comprises:
   a first portion fixed to an inner surface of the tube, and
   a second portion fixed to an outer surface of the twisting wire, the second portion being fitted to the first portion.

12. The actuator according to claim 11, wherein
   the first portion extends in the longitudinal direction of the tube and has an interior with a first non-circular cross sectional shape, and
   the second portion extends in the longitudinal direction of the tube and has an exterior with a second cross sectional shape,
   wherein the first non-circular cross sectional shape of the first portion is fitted to the second cross sectional shape of the second portion.

* * * * *